(12) United States Patent
Sanders

(10) Patent No.: US 8,953,157 B2
(45) Date of Patent: Feb. 10, 2015

(54) MONOLITHIC FIBER OPTIC SENSOR ASSEMBLY

(75) Inventor: Scott Sanders, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 122 days.

(21) Appl. No.: 13/363,490

(22) Filed: Feb. 1, 2012

(65) Prior Publication Data
US 2013/0194571 A1  Aug. 1, 2013

(51) Int. Cl.
*G01J 3/00* (2006.01)
*G02B 6/00* (2006.01)

(52) U.S. Cl.
CPC .... *G02B 6/00* (2013.01); *G01J 3/00* (2013.01)
USPC ........................................................ 356/300

(58) Field of Classification Search
USPC ....................... 356/300, 153, 498; 385/12, 96; 73/31.05; 355/67; 372/6
See application file for complete search history.

(56) References Cited

U.S. PATENT DOCUMENTS

| | | | | |
|---|---|---|---|---|
| 4,509,827 | A * | 4/1985 | Cowen et al. | 356/153 |
| 4,892,383 | A * | 1/1990 | Klainer et al. | 385/12 |
| 6,593,998 | B2 * | 7/2003 | Gruner et al. | 355/67 |
| 2009/0022457 | A1 * | 1/2009 | de Jong et al. | 385/96 |
| 2011/0170116 | A1 * | 7/2011 | Homa et al. | 356/498 |
| 2011/0268141 | A1 * | 11/2011 | Nakatate | 372/6 |
| 2012/0006098 | A1 * | 1/2012 | Degner et al. | 73/31.05 |

* cited by examiner

*Primary Examiner* — Tarifur Chowdhury
*Assistant Examiner* — Jamil Ahmed
(74) *Attorney, Agent, or Firm* — Boyle Fredrickson, S.C.

(57) ABSTRACT

A remote sensor element for spectrographic measurements employs a monolithic assembly of one or two fiber optics to two optical elements separated by a supporting structure to allow the flow of gases or particulates therebetween. In a preferred embodiment, the sensor element components are fused ceramic to resist high temperatures and failure from large temperature changes.

18 Claims, 4 Drawing Sheets

MONOLITHIC FIBER OPTIC SENSOR ASSEMBLY

STATEMENT REGARDING FEDERALLY SPONSORED RESEARCH OR DEVELOPMENT

This invention was made with government support under DE-EE0000202 awarded by the US Department of Energy. The government has certain rights in the invention.

CROSS REFERENCE TO RELATED APPLICATION

* * *

BACKGROUND OF THE INVENTION

The present invention relates to instruments for the study of gases or particle laden fluids and in particular to an improved sensor system for providing spectrographic information about high-temperature or corrosive environments.

Remote spectrographic measurements may be made using a fiber optic guide attached to a "U-bench" being an optical component supporting an opposed light emitter and light collector or an opposed light emitter and mirror across a gap. Gases to be analyzed may pass freely within the gap to absorb frequencies of the light creating a spectrographic signature.

Precise alignment of the optical elements of the U-bench is normally obtained by close tolerance machining augmented by a separate alignment step where minor adjustments to the optical elements are made and then the optical elements fixed in a curing polymer such as epoxy. This two-step process allows a precision exceeding that obtained with normal mechanical tolerances alone.

Knowledge about gaseous species can be important in the study and control of chemical reactions in high-temperature environments including internal combustion engines, coal gasifiers in power plants, or gases in high-temperature process furnaces. The epoxies used in constructing a typical sensor U-bench are normally not compatible with such high temperatures or corrosive environments. For this reason, construction of U-bench type sensors for these applications can be time consuming and expensive.

SUMMARY OF THE INVENTION

The present invention provides a high temperature U-bench constructed of a monolithic optical ceramic material. Two opposed lenses or an opposed lens and mirror together with the supporting structure of the U-bench are constructed of compatible materials and fused together to provide a system robust against high temperatures and wide temperature swings that might otherwise affect precision optical alignment or cause mechanical failure.

In one embodiment, the invention provides a monolithic sensor assembly including an elongate member extending along an extension axis between a first and second end and having an opening between the first and second ends for passage of fluid material therethrough, and a light guiding element fusibly attached to the elongate member at the first end, the light guiding element having an optical axis generally parallel to the extension axis. A light receiving element is fusibly attached to the elongate member at the second end, the light receiving element having an optical axis aligned with the optical axis of the light guiding element and being spaced from the light guiding element by a region of the elongate member having the opening. At least one optical fiber is then fusibly attached to one of the light guiding element and light receiving element to receive light passing between the light guiding element and light receiving element through the fluid material.

It is thus a feature of at least one embodiment of the invention to provide a monolithic optical sensor assembly in which the components are fused together to better resist high temperature environments.

The elongate member and the light guiding element and light receiving element may be composed of at least one ceramic material selected from the group consisting of crystalline and amorphous ceramics.

It is thus a feature of at least one embodiment of the invention to construct the monolithic sensor of compatible materials providing the desirable resistance to high temperature and corrosive environments.

At least one ceramic material is selected from the group consisting of sapphire, silica glass, and zirconia.

It is thus a feature of at least one embodiment of the invention to provide a sensor that may be fabricated out of readily available high-temperature materials.

The elongate member and the light guiding element and light receiving element may be composed of an identical ceramic material.

It is thus a feature of at least one embodiment of the invention to provide a monolithic structure that maintains optical alignment and integrity with extreme swings in temperature.

The ceramic materials may be transparent.

It is thus a feature of at least one embodiment of the invention to provide a monolithic sensor in which light transmitting optical elements may be fused to compatible support structure.

The elongate member may be a substantially cylindrical tube and the light guiding element and light receiving element may provide cylindrical peripheries coaxially fitting into ends of the tube to be fused thereto.

It is thus a feature of at least one embodiment of the invention to provide a simple mechanical self-alignment method suitable for use with standard ceramic shapes.

The light guiding element may be a lens having an optical axis defining the optical axis of the light guiding element and the light receiving element may be a mirror substrate having a mirror surface defining an optical axis of the light receiving element.

It is thus a feature of at least one embodiment of the invention to provide a sensor that may be tethered at only one end by optical fibers simplifying its placement in use.

The mirror may be a dielectric mirror.

It is thus a feature of at least one embodiment of the invention to provide a mirror surface that may withstand high temperatures by being constructed of two or more high-temperature dielectrics of different indices of refraction without the risk of possibly corroding metallic mirror surfaces.

The mirror surface may have a concave surface facing the lens for optical focusing of light.

It is thus a feature of at least one embodiment of the invention to provide improved light return for higher signal-to-noise ratio.

The lens may have a diameter of greater than 0.5 mm and the optical fiber may have a diameter substantially less than 0.25 mm.

It is thus a feature of at least one embodiment of the invention to provide a broad area collimated beam from a narrow single mode fiber for increasing the interaction between light and the fluid material to be measured.

The lens may have a convex surface facing the mirror for optical collimation of light.

It is thus a feature of at least one embodiment of the invention to provide improved beam area and capture of returned light.

These particular objects and advantages may apply to only some embodiments falling within the claims and thus do not define the scope of the invention.

DETAILED DESCRIPTION OF THE PREFERRED EMBODIMENT

Figure 1:
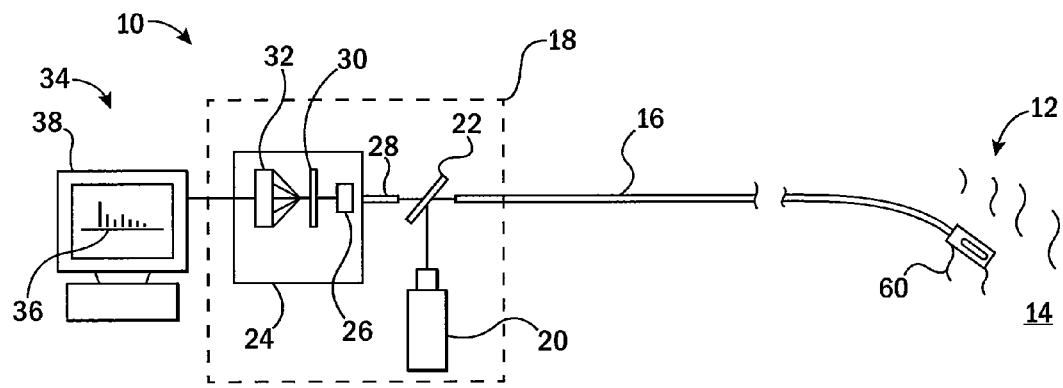
FIG. 1 is a simplified schematic representation of a spectrographic system employing the sensor of the present invention.

Referring now to FIG. 1, a spectrographic system 10 may include a sensor head 12 that may fit within a high temperature gaseous environment 14 and communicate via a fiber optic light guide 16 having one or more optical fibers with a remote spectrometer 18.

The spectrometer 18, in one embodiment, may include a polychromatic light source 20 providing a broad spectrum light output, for example, using an incandescent bulb in the form of a quartz tungsten-halogen lamp, or a wideband light emitting diode (LED), or broadband laser, each providing substantial energy, for example, in the range of 1000 nanometers to 3000 nanometers and preferably in the range of 1330 nanometers to 1360 nanometers and having a known spectral profile. The polychromatic light source 20 may direct a light beam to a beam splitter 22 or other similar device that in turn directs the light into the fiber optic light guide 16.

Generally, light passing through into fiber optic light guide 16 from the polychromatic light source 20 travels to the sensor head 12 to interact with the gas 60 of the gaseous environment 14 and to return along fiber optic light guide 16 where it is again received by the beam splitter 22 this time to pass to a spectrometer 24.

The spectrometer 24 may be, for example, a slit spectrometer providing a slit assembly 26 (possibly formed by a portion of fiber-optic 28 communicating with the beam splitter 22) and any necessary collimating optics followed by an optical grating 30, the latter projecting a spectrum on a digital camera 32 or the like. The digital camera 32 may, for example, include a solid-state image detector 32 such as an InGaAs line scan camera commercially available from Xenics Leuven, Belgium. The spectrum may be analyzed by a computer 34 according to techniques known in the art to display absorption bands 36 or the like on a display terminal 38. For example, the computer processing may compare a spectral profile of the received light to a known spectral profile of the transmitted light from the polychromatic light source 20. Other measurements of this type well known in the art may be conducted by the spectrometer 24 and other forms of spectrometer 24 may also be employed including, for example, those described in U.S. Pat. No. 7,826,061 assigned to the same assignee as the present invention and hereby incorporated by reference.

Figure 2:
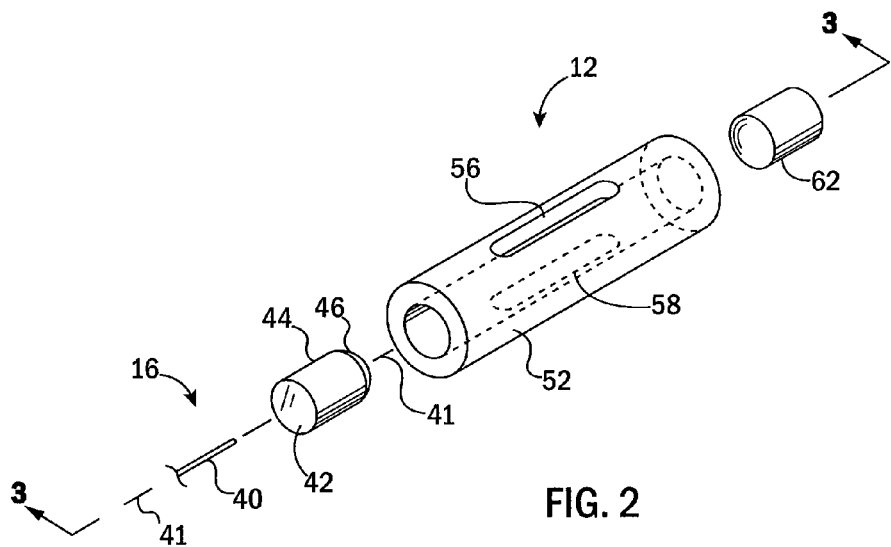
FIG. 2 is an exploded perspective view of the elements of one embodiment of the sensor of the present invention prior to assembly including a lens, elongate support, mirror, and optical fiber.
Figure 3:
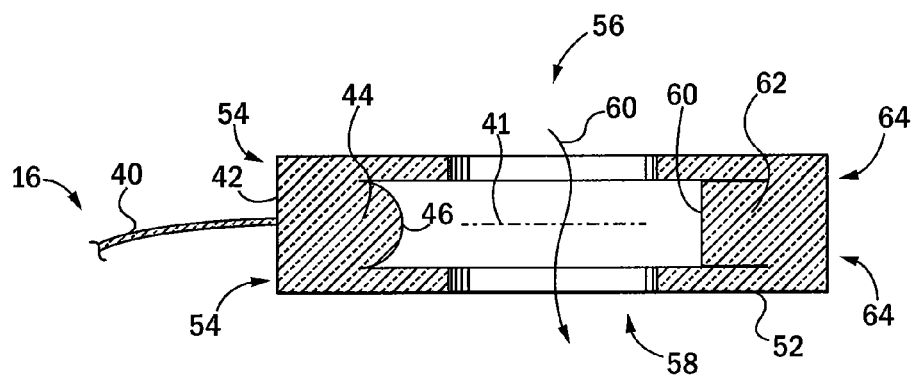
FIG. 3 is a cross-section along line 3-3 of FIG. 2 showing the sensor after assembly of the elements by fusing.

Referring now to FIGS. 2 and 3, the fiber optic light guide 16 attached to the sensor head 12 may be, in one embodiment, a single, single mode fiber 40, attached at a center of a rear planar surface 42 of a cylindrical body of a lens 44 to be generally perpendicular thereto and aligned with the optical axis 41, perpendicular to a plane of the rear planar surface 42, at the point of attachment. The lens 44 provides a light receiving element for the sensor head 12.

Figure 4:
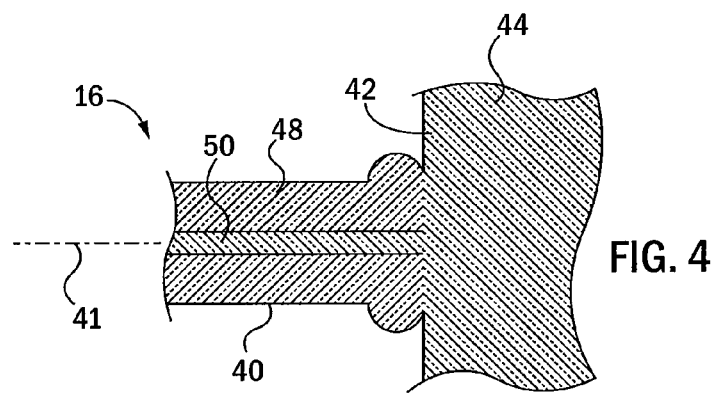
FIG. 4 is a detailed fragmentary view of FIG. 3 showing the attachment of the optical fiber to the lens.

Referring momentarily to FIG. 4, the single mode fiber 40 may provide for an outer cladding 48 surrounding an inner core 50 of different indices of refraction as is understood in the art. Typically, for the frequencies of interest described above, the core 50 will have a diameter of 20 micrometers or less and typically 10 micrometers or less while the cladding 48 will have a diameter significantly greater than 20 micrometers but less than 0.25 millimeters and typically of substantially 125 micrometers. In contrast, the cylindrical body of the lens 44 may have a diameter of greater than 0.5 millimeters and typically on the order of 1.2 millimeters.

The attachment between the optical fiber 40 and the rear planar surface 42 of the lens 44 may be performed by fusing the two together by partial melting of each to an integrated monolithic structure with the material of the core 50 communicating directly to material of the lens 44. Preferably, each of the materials of the core 50 and lens 44 will have similar indices of refraction. It will be appreciated that some mismatch between the materials of the core 50 and lens 44 may be accommodated by providing an angled interface (with respect to the direction of light propagation) that accommodates the difference in indices of refraction according to techniques well known in the art. This same technique may be used with other interfaces between optical fibers and optical elements of the sensor head 12 described below.

Referring again to FIGS. 2 and 3, the cylindrical body of the lens 44 may be inserted into a support structure 52 preferably comprising a cylindrical tube extending along the axis 41 and having a bore diameter substantially equal to the outer diameter of the cylindrical body of the lens 44. In this way the lens of 44 may slide into the support structure 52 at one end, while maintaining alignment between an optical axis of the lens 44 and axis 41. Once inserted into the tubular support structure 52, the lens 44 may be fused to the support structure 52 at zones 54 along an exposed interface between the tubular support structure 52 and cylindrical body of the lens 44. This fusing may be performed by melting the materials of the support structure 52 and lens 44 together at the interface into a monolithic structure.

A face of the cylindrical body of the lens 44 received within the support structure 52 and opposite rear planar surface 42 may provide a lens surface 46 being outwardly convex and having an optical axis aligned with axis 41 to collimate light received from the optical fiber 40 into a wider beam directed along the axis 41 into the support structure 52.

The support structure 52 may provide for a transverse passageway formed by openings 56 and 58 positioned across from each other along an axis perpendicular to the optical axis 41. Openings 56 and 58 provide a channel allowing the passage of gas 60, including species to be analyzed, across the optical axis 41 to receive light collimated and directed outward into the gas 60 by the lens surface 46.

An opposite end of the support structure 52 may receive a cylindrical mirror substrate 62 also having an outer diameter approximately equal to the bore diameter of the tubular support structure 52 so that the mirror substrate 62 may slide into the opposite end of the tubular support structure 52 maintaining its alignment with the axis 41 and then fused to the support structure 52 at zones 64 at an exposed interface between the support structure 52 and the cylindrical mirror substrate 62.

A front face of the cylindrical mirror substrate 62 facing the lens surface 46, may provide for an outwardly planar mirror surface 66, for example, using layered high temperature dielectric materials to create a dielectric mirror or a metallic layer to create a conventional mirror. The planar shape of the mirror surface 66 has an optical axis (surface normal) aligned with axis 41 to return light received from the lens surface 46 back along the optical axis 41 to the lens surface 46 for receipt thereby. A concave shape of the mirror surface 66 may be desirable when the lens 44 is replaced by a window as will be described below. The mirror formed by the cylindrical mirror substrate 62 and the mirror surface 66 provides a light receiving element.

It will be appreciated that the components of the sensor head 12 may thus be mechanically assembled and retained by fusing without the need for heat-susceptible epoxy materials. In a preferred assembly technique, the lens 44 and cylindrical mirror substrate 62 are first assembled to the tubular support structure 52 with alignment with optical axis 41 promoted by the interfacing surfaces of these elements. These elements are then fused together. The optical fiber 40 may then be abutted without fusing against the rear planar surface 42 of the cylindrical body of the lens 44 and light transmitted through the optical fiber 40 to the lens 44. The light received from the optical fiber 40 from the lens 44 is measured and the position of the optical fiber 40 adjusted to maximize that return of the light into the optical fiber 40 prior to fusing of the fiber 40 to the rear planar faces 42. Upon proper positioning of the fiber 40, the fusing process may be performed, for example, by an arc heat source as will be described below.

In a preferred embodiment, each of the components of the sensor head 12 described including the fiber 40, the lens 44, the tubular support structure 52 and the mirror substrate 62 are constructed of a high temperature ceramic material, defined broadly herein as including both crystalline and amorphous ceramics. In one embodiment, each of the ceramics may be identical to provide both for compatibility for the fusing operation and to provide for similar coefficients of expansion to preserve optical alignment during radical temperature changes and eliminate possibly destructive stress. In any case, the coefficients of expansion for these different components may be matched for this purpose even when different materials are used. The ceramic materials may further all be transparent. Suitable ceramic materials include sapphire, silica glass, and zirconia, although other ceramics may also be used. Silica glass, also known as fused quartz, is a substantially pure silicon dioxide in contrast to soda-lime glass having ingredients such as sodium carbonate and calcium oxide.

When silica glass is used, the sensor head 12 may withstand temperatures up to 1400 degrees Kelvin and provides a functional lifetime that may extend to decades without the need for replacement.

Figure 5:
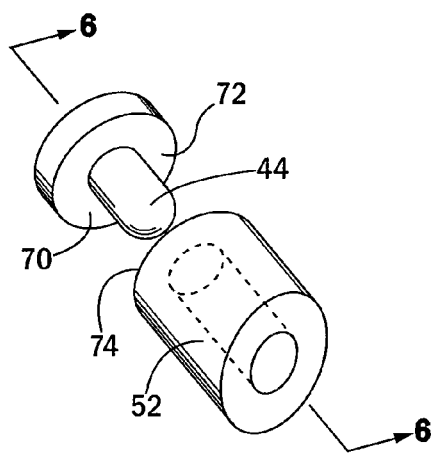
FIG. 5 is a fragmentary perspective view of one end of the elongate support with an alternative lens design having a flange for simplified manufacturing.
Figure 6:
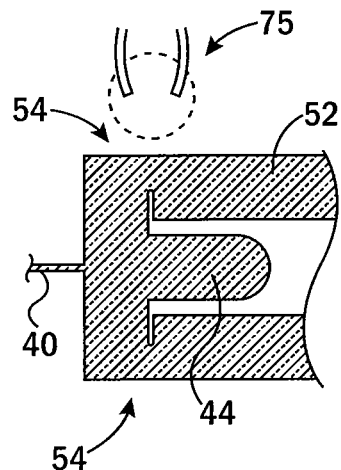
FIG. 6 is a cross-sectional view along line 6-6 of FIG. 5 showing the fusing of the flange using an electric arc.

Referring now to FIG. 5, fusing of the lens 44 and support structure 52 may be simplified by the addition of a radially extending flange 70 from a rear end of the cylindrical body of the lens 44 to provide a front radial surface 72 which may abut a rear radial surface 74 of the tubular support structure 52. In this case an electrical arc 75 or similar heat source may be applied around the periphery of the tube of the support structure 52 to fuse the lens 44 to the support structure 52 in zones 54 removed from the fiber 40. A similar configuration using the flange 70 may be used for the mirror substrate 62 or for dual lenses 44 and 76 to be described below.

Figure 7:
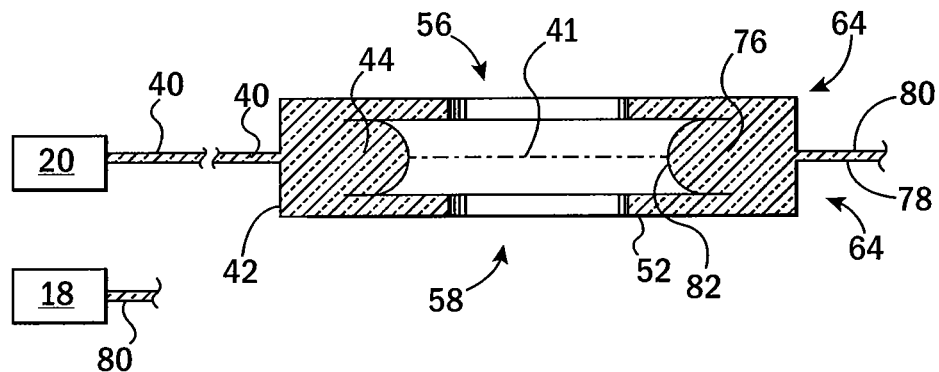
FIG. 7 is a figure similar to that of FIG. 3 showing an alternative embodiment providing for two fiber elements on opposed lenses.

Referring now to FIG. 7, in an alternative embodiment, the mirror substrate 62 may be replaced with a second lens 76 being substantially identical to lens 44 but rotated to face lens 44 and having its optical axis also aligned with optical axis 41. Lens 76, like mirror substrate 62, is fused to the support structure 52 in zones 64 and presents rear planar surface 78 corresponding to rear planar surface 42 to which a second optical fiber 80 may be attached. In this case optical fiber 40 may connect with the polychromatic light source 20 to provide light through lens 44 along the optical axis 41 to be received by lens 76 which may communicate that light to fiber 80 which may be received by the spectrometer 18. This approach eliminates light loss inherent in beam splitter 22 shown in FIG. 1. The lens 76 thereby provides an alternative light receiving element.

The lens 76 may be manufactured as described with respect to FIG. 5 and may be constructed of the same material as lens 44 and include a lens surface 82 collimating light received from cylindrical body of the lens 76 for receipt through fiber 80. Fiber 80 may be attached to the lens 76 in a similar manner described above with respect to fiber 40, for example, by mechanically positioning and fusing fiber 40 close to the optical axis 41 and adjusting fiber 80 interactively by measuring the light received by fiber 80 from fiber 40 to obtain maximum light throughput. Fiber 80 may then be fused to rear planar surface 78.

Figure 8:
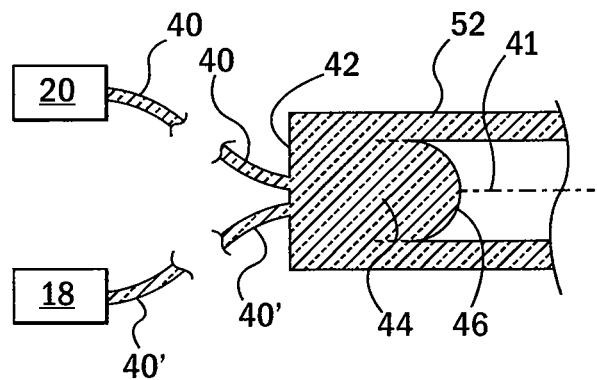
FIG. 8 is a figure similar to that of FIG. 3 showing the attachment of two optical fibers to a single lens opposed to a mirror.

Referring now to FIG. 8, the embodiment of FIG. 2 may be modified to eliminate the need for a beam splitter 22 by attaching two optical fibers 40 and 40' to the rear planar surface 42 close to the optical axis 41. Fiber 40 may communicate to the polychromatic light source 20 while fiber 40' may lead to the spectrometer 18. Alignment of the fibers 40 and 40' may be done by holding them in a predetermined spaced apart relationship and moving the centerline of the fibers 40 and 40' together while measuring the light received from fiber 40' with illumination of the fiber 40 to maximize that former value as described above.

Figure 9:
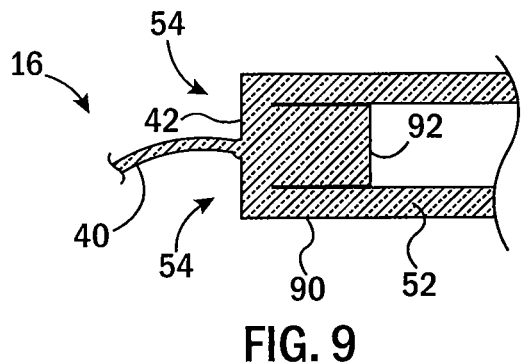
FIG. 9 is a figure similar to that of FIG. 8 showing the replacement of the convex lens with a planar lens or window element.

Referring now to FIG. 9, the lens 44 may be replaced with a window 90 (being essentially a lens 44 with a planar lens surface 46) having a planar face 92 opposite the rear planar surface 42 the latter which provides the connection to the fiber 40 as before. The planar face 92 simplifies the fabrication of the device and providing an achromatic optical element (operating at multiple light frequencies).

Figure 10:
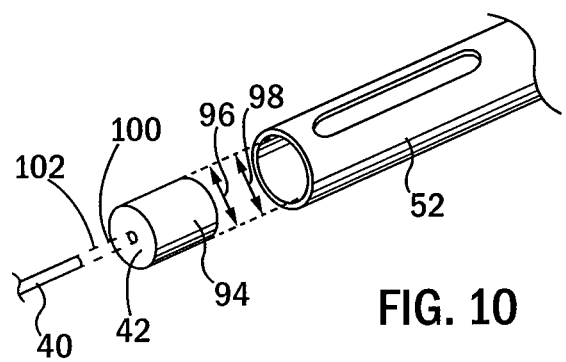
FIG. 10 is a fragmentary perspective view similar to that of FIG. 2 showing assembly of elements of a fiber and support to provide a window assembly.
Figure 11:
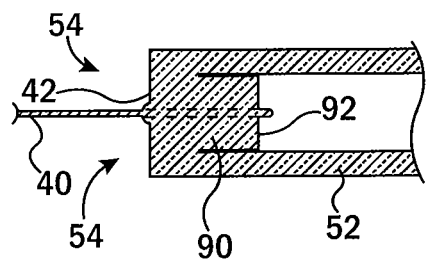
FIG. 11 is a fragmentary cross-section similar to FIG. 9 of the embodiment of FIG. 10 showing the fusing of the elements.

Referring now to FIGS. 10 and 11, in yet a further embodiment, the window 90 of FIG. 9 may be fabricated through the use of a tubular centering element 94 having an outer diameter 96 substantially equal to the inner diameter 98 of the tubular support structure 52 as described above with respect to FIG. 2. The tubular centering element 94 may have an inner diameter 100 equal to the outer diameter 102 of the light fiber 40. The light fiber 40 may be inserted into the tubular centering element 94 and the two fused together to be monolithic while preserving the interface between different indices of refraction allowing light to be conducted through the window 90 formed by the fusing of tubular centering element 94 and fiber 40 to the front surface 92. The fused tubular centering element 94 and fiber 40 are then inserted into the support structure 52 and a second fusing operation is conducted at regions 54 as described above. Or these two fusing processes may be conducted simultaneously. The natural surface tension induced contraction of the tubular centering element 94 when fused to the fiber 40 preserves the necessary alignment for this unfocused version. Alternatively an alignment step may be conducted by manipulating the window formed by the fused tubular centering element 94 and fiber 40 within the support structure 52 prior to fusing therein.

It will be appreciated that the present invention need not be used with a polychromatic light source but may instead be used with a swept monochromatic light source. The term "optical element" as used herein should be understood to include generally lenses, mirrors and windows that transmit, reflect or refract a light beam and that may, but need not, cause convergence or divergence of the light beam.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What I claim is:

1. A sensor monolithic assembly comprising:
   (a) an elongate member extending along an extension axis between a first and second end and having a first and second opening positioned between the first and second ends to provide a channel allowing for passage of fluid material therethrough;
   (b) a light guiding element fusibly attached to the elongate member at the first end, the light guiding element directing light along a first optical axis generally parallel to the extension axis, and
   (c) a mirror substrate fusibly attached to the elongate member at the second end, the mirror substrate having a second optical axis aligned with the first optical axis and being spaced from the light guiding element by a region of the elongate member having the first and second openings; and
   an optical fiber fusibly attached to the light guiding element to receive light passing between the light guiding element and the mirror substrate through the fluid material;
   wherein the elongate member, the light guiding element and the mirror substrate are materials having substantially the same coefficients of expansion and are fusibly attached by melting, and
   wherein the light passing between the light guiding element and the mirror substrate through the fluid material is received through an area of the optical fiber that is fused to the light guiding element.

2. The sensor assembly of claim 1 wherein the elongate member and the light guiding element and the mirror substrate are composed of at least one ceramic material selected from the group consisting of crystalline and amorphous ceramics.

3. The sensor assembly of claim 2 wherein at least one ceramic material is selected from the group consisting of sapphire, silica glass, and zirconia.

4. The sensor assembly of claim 2 wherein the elongate member and the light guiding element and the mirror substrate are composed of an identical ceramic material.

5. The sensor assembly of claim 2 wherein at least one ceramic material is transparent.

6. The sensor assembly of claim 1 wherein the elongate member is a substantially cylindrical tube and wherein the light guiding element provides a cylindrical periphery coaxially fitting into the first end of the tube to be fused thereto.

7. The sensor assembly of claim 1 wherein the light guiding element is a lens having an optical axis defining the first optical axis and the mirror substrate provides a mirror surface defining the second optical axis.

8. The sensor assembly of claim 7 wherein the mirror is a dielectric mirror.

9. The sensor assembly of claim 7 wherein the mirror surface has a concave surface facing the lens for optical focusing of light.

10. The sensor assembly of claim 7 wherein the lens has a diameter of greater than 0.5 mm and the optical fiber has a diameter substantially less than 0.25 mm.

11. The sensor assembly of claim 7 wherein the lens has a convex surface facing the mirror for optical collimation of light.

12. The sensor assembly of claim 1 wherein the optical fiber has a core diameter of less than 30 µm.

13. The sensor assembly of claim 1. wherein the optical fiber has a core diameter of less than 10 µm.

14. The sensor assembly of claim 1 wherein the optical fiber is a single mode optical fiber.

15. The sensor assembly of claim 1 wherein the first and second optical axes pass through an area of the optical fiber that is fused to the light guiding element.

16. A method of manufacturing an optical sensor of a type having:
- (a) an elongate member extending along an extension axis between a first and second end and having a first and second opening positioned between the first and second ends to provide a channel allowing for passage of fluid material therethrough;
- (b) a light guiding element fusibly attached to the elongate member at the first end, the light guiding element oriented to direct light along a first optical axis generally parallel to the extension axis, and
- (c) a mirror substrate fusibly attached to the elongate member at the second end, the mirror substrate having a second optical axis aligned with the first optical axis and being spaced from the light guiding element by a region of the elongate member having the first and second openings, wherein the elongate member, the light guiding element and the mirror substrate are materials having substantially the same coefficients of expansion and are fusibly attached by melting; and a single mode optical fiber fusibly attached to the light guiding element to receive light passing between the light guiding element and the mirror substrate through the fluid material;

the method comprising the steps of:
- (a) fusing the light guiding element and the mirror substrate to the elongate support by mutual inciting of portions of the light guiding element and the mirror substrate and elongate support so that the first and second optical axes are aligned and generally parallel to the extension axis of the elongate support; and
- (b) fusing the optical fiber to the light guiding element so that the light passing between the light guiding element and the mirror substrate through the fluid material is received through an area of the optical fiber that is fused to the light guiding element.

17. The method of claim 16 including before step (b) and after step (a) the step of positioning the optical fiber against a rear surface of light guiding element away from the mirror substrate while measuring an intensity of light received into the optical fiber from the light guiding element from light passing between the light guiding element and the mirror substrate to maximize that received light and fusing the optical fiber to the light guiding element by mutual melting of portions of the light guiding element and optical fiber as so positioned.

18. The method of claim 16 wherein the light guiding element is a tube having an outer diameter substantially equal to an inner diameter of one end of the elongate member and having an inner diameter substantially equal to an outer diameter of the optical fiber and including the step of inserting the optical fiber into the light guiding element before step (b).

* * * * *

UNITED STATES PATENT AND TRADEMARK OFFICE
CERTIFICATE OF CORRECTION

PATENT NO.         : 8,953,157 B2                                        Page 1 of 1
APPLICATION NO.    : 13/363490
DATED              : February 10, 2015
INVENTOR(S)        : Scott Sanders It is certified that error appears in the above-identified patent and that said Letters Patent is hereby corrected as shown below:

IN THE CLAIMS

CLAIM 1, Col. 8, Line 12, delete "member haying the first and second" and substitute therefore
-- member having the first and second --

CLAIM 16, Col. 9, Line 27, delete "support by mutual inciting" and substitute therefore
-- support by mutual melting --

Signed and Sealed this
Ninth Day of June, 2015

Michelle K. Lee
*Director of the United States Patent and Trademark Office*